United States Patent
Bhowmick et al.

(10) Patent No.: US 12,268,380 B2
(45) Date of Patent: Apr. 8, 2025

(54) SCAFFOLD DEVICES, SYSTEMS, AND METHODS FOR TISSUE TRACTION

(71) Applicant: Boston Scientific Limited, Hamilton (BM)

(72) Inventors: Nabarun Bhowmick, Kolkata (IN); Deepak K. Sharma, Muzaffarnagar (IN); Shrikant V. Raut, Mumbai (IN)

(73) Assignee: BOSTON SCIENTIFIC MEDICAL DEVICE LIMITED, Galway (IE)

( * ) Notice: Subject to any disclaimer, the term of this patent is extended or adjusted under 35 U.S.C. 154(b) by 0 days.

(21) Appl. No.: 17/554,700

(22) Filed: Dec. 17, 2021

(65) Prior Publication Data
US 2022/0192648 A1    Jun. 23, 2022

Related U.S. Application Data

(60) Provisional application No. 63/128,938, filed on Dec. 22, 2020.

(51) Int. Cl.
*A61B 17/02*    (2006.01)

(52) U.S. Cl.
CPC .. *A61B 17/0218* (2013.01); *A61B 2017/0287* (2013.01)

(58) Field of Classification Search
CPC .............. A61B 1/0014; A61B 17/0218; A61B 17/0293; A61B 17/0206; A61B 2017/0287; A61B 1/018; A61B 2017/0225; A61B 17/0281; A61F 2/01; A61F 2/0103; A61F 2/06; A61F 2/848; A61F 2/82
See application file for complete search history.

(56) References Cited

U.S. PATENT DOCUMENTS

| 5,582,577 | A | * | 12/1996 | Lund | .................. | A61B 17/0218 600/233 |
| 2,123,227 | A1 | * | 11/2009 | Yamatani | ........... | A61B 17/0218 600/104 |

(Continued)

OTHER PUBLICATIONS

Fold—definition of fold by the Free Dictionary, https://www.thefreedictionary.com/fold, accessed on Sep. 12, 2022 (Year: 2022).*

(Continued)

*Primary Examiner* — Jan Christopher L Merene
(74) *Attorney, Agent, or Firm* — Seager, Tufte & Wickhem, LLP

(57) ABSTRACT

A tissue traction device including a scaffold structure configured to anchor the tissue traction device in place such that a tissue traction element is anchored upon deployment of the scaffold structure and without further manipulation of the tissue traction device (such as to grasp tissue or otherwise anchor the tissue traction element to tissue). The scaffold structure may be self-supporting/self-standing to be in a deployed expanded configuration to anchor the tissue traction device with respect to the tissue. The tissue traction element may be pivotably coupled to the scaffold structure, such as to a rigid element of the scaffold structure. The tissue traction element, when anchored by the scaffold, exerts a force (e.g., traction force) on a region of target tissue to which the tissue traction element is coupled, such as via a tissue engagement member.

20 Claims, 8 Drawing Sheets

(56) References Cited

U.S. PATENT DOCUMENTS

| | | |
|---|---|---|
| 10,206,669 B2 | 2/2019 | Bhatt et al. |
| 2005/0043757 A1* | 2/2005 | Arad .................... A61B 17/083 |
| | | 606/200 |
| 2009/0018396 A1* | 1/2009 | Takizawa ........... A61B 1/00147 |
| | | 600/127 |
| 2012/0041291 A1* | 2/2012 | Ferren .................... A61B 10/04 |
| | | 604/95.01 |
| 2017/0105726 A1* | 4/2017 | Smith .................... A61B 17/28 |
| | | 606/139 |
| 2018/0035997 A1* | 2/2018 | Smith .................. A61B 17/122 |
| 2018/0263614 A1 | 9/2018 | Lee et al. |
| 2019/0099172 A1 | 4/2019 | Wales et al. |
| 2019/0167950 A1* | 6/2019 | Weitzner ........... A61M 25/0138 |
| | | 600/204 |
| 2019/0201670 A1* | 7/2019 | Napolez .............. A61J 15/0015 |
| 2019/0223710 A1* | 7/2019 | Tilson ..................... A61B 1/32 |
| 2020/0046217 A1* | 2/2020 | Butcher .................. A61B 1/32 |
| | | 600/114 |
| 2020/0178948 A1* | 6/2020 | Piskun ............... A61B 17/0206 |
| | | 600/205 |
| 2020/0360005 A1 | 11/2020 | Rodriguez Salazar et al. |

OTHER PUBLICATIONS

"Clearer Visualization Simplified Dissection," Medtronic, 2 pgs., (2021).
"ProdiGi Traction Wire," Medtronic, 4 pgs., (2021).

\* cited by examiner

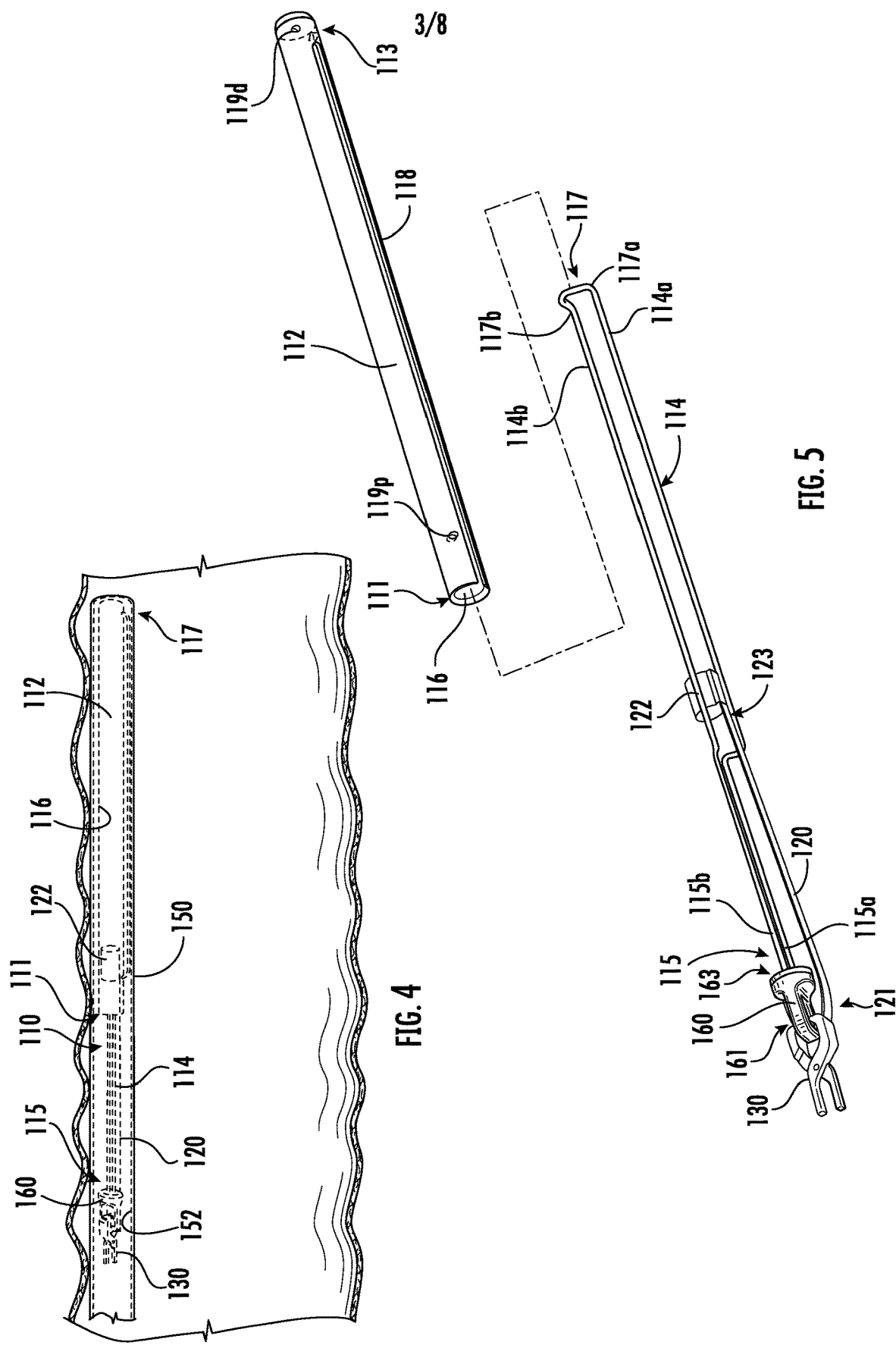

SCAFFOLD DEVICES, SYSTEMS, AND METHODS FOR TISSUE TRACTION

PRIORITY

The present application is a non-provisional of, and claims the benefit of priority under 35 U.S.C. § 119 to, U.S. Provisional Application Ser. No. 63/128,938, filed Dec. 22, 2020, the disclosure of which is hereby incorporated herein by reference in its entirety for all purposes.

FIELD

The present disclosure relates generally to the field of devices, systems, and methods for applying traction to tissue.

BACKGROUND

Various endoscopic surgical procedures require maneuvering about various anatomical structures. Some procedures, such as endoscopic mucosal resection (EMR), Endoscopic Submucosal Dissection (ESD), Pre-Oral Endoscopic Myotomy (POEM), etc., allow for minimally invasive endoscopic removal of benign and early malignant lesions, such as in the gastrointestinal (GI) tract. Because such procedures are minimally invasive, there is limited space to maneuver within the body. In procedures involving cutting of tissue, the loose section of tissue may obstruct visibility, such as by falling on the endoscope, occluding visibility of the camera, and creating a hindrance affecting movement of the instruments used during the procedure and in reaching the extreme corners of the target tissue being cut. Various solutions for lifting the hanging mass of tissue, thus clearing the path for visibility and operation of medical tools and devices, have been developed. However, positioning and maneuvering the elements used with such solutions may be challenging. Also, the elements used with such solutions may require separate medical tools than those used to perform the procedure, and such tools may even require a separate working channel in the endoscope, thereby potentially increasing the size and/or complexity of the endoscope. Alternative solutions for lifting tissue during a procedure which reduce cost, complexity, and cognitive load presented by currently available solutions would be welcome.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, in one aspect a tissue traction device is provided with a self-supporting scaffold configured to be anchored with respect to tissue surrounding a region of target tissue upon expansion and contact with the tissue; and a tissue traction element having a first end coupled to the scaffold, and a second end free to be coupled to the region of target tissue, the tissue traction element being anchored with respect to the region of target tissue by the self-supporting scaffold. In one aspect, the scaffold includes a wire structure and a rigid element.

In some embodiments, the wire structure is configured to bow away from the rigid element, the wire structure engaging a first region of the tissue and the rigid element engaging a second region of the tissue spaced apart from the first region to anchor the tissue traction device with respect to the tissue. In some embodiments, the wire structure is movable with respect to the rigid element between an elongated configuration in which the tissue traction device is in a collapsed delivery configuration for fitting within a lumen of a delivery device, and a bowed configuration extending away from the rigid element when the tissue traction device is in an expanded deployed configuration. In some embodiments, the rigid element includes a wall defining a lumen therein; the wire structure extends through a proximal end of the rigid element into the lumen thereof, through a proximal aperture adjacent a proximal end of the rigid element wall, along a length of the rigid element, and through a distal aperture adjacent a distal end of the rigid element wall, the wire structure having a distal end secured within the lumen in the rigid element adjacent the distal end of the rigid element; and the wire structure is shiftable from an elongated configuration extending along the rigid element and partially within the lumen of the rigid element, to a bowed configuration flexing away from the rigid element along a portion of the wire structure extending outwardly from the rigid element between the proximal aperture and the distal aperture in the rigid element wall. In some embodiments, the wire structure includes first and second legs, each of the legs extending through the proximal end of the rigid element into the lumen thereof, through a respective proximal aperture in the rigid element wall, along a length of the rigid element, and through a respective distal aperture in the rigid element wall, the legs of the wire structure each having a distal end secured within the lumen in the rigid element adjacent the distal end of the rigid element.

In some embodiments, the wire structure includes a first section engaging a first region of the tissue and a second section engaging a second region of the tissue spaced apart from the first region, the first section and the second section biased apart to anchor the tissue traction device with respect to the tissue. In some embodiments, the rigid element is pivotably coupled to a distal end of the wire structure, and a biasing element biases the rigid element in a distal direction away from the wire structure.

In accordance with various principles of the present disclosure, the tissue traction element is elastic and pivotably coupled with respect to a portion of the scaffold. In some embodiments, the tissue traction element extends from the rigid element. In some embodiments, the rigid element is tubular and defines a lumen therein; and the first end of the tissue traction element is coupled to the rigid element within the lumen defined in the rigid element. In some embodiments, the first end of the tissue traction element is coupled to a first end of the rigid element; a second end of the rigid element is coupled to a distal end of the wire structure; and a biasing element is positioned with respect to the second end of the rigid element and the wire structure to bias the rigid element and the tissue traction element in a distal direction away from the wire structure.

In accordance with various additional or alternative principles of the present disclosure, the scaffold is shiftable between a collapsed delivery configuration sized to fit within a lumen of a delivery device and an expanded deployed configuration sized to engage the tissue to anchor the tissue traction device with respect to the tissue. In some embodiments, the scaffold shifts from a longitudinally extended delivery configuration to a flexed expanded deployed configuration. In some embodiments, the scaffold shifts from a folded delivery configuration to the expanded deployed configuration.

In accordance with various principles of the present disclosure, in another aspect, a tissue traction system includes a delivery device defining a lumen therethrough; a scaffold configured to be anchored with respect to tissue surrounding a region of target tissue upon contact with the target tissue by shifting from a collapsed delivery configuration sized to fit within the delivery device lumen to an expanded deployed configuration sized to engage the tissue to anchor the tissue traction device with respect to the tissue; a tissue engagement member configured to grasp the region of target tissue; and a tissue traction element having a first end coupled to the scaffold, and a second end free to be coupled to the region of target tissue by the tissue engagement member.

In some embodiments, the scaffold includes a wire structure resilient to shift between an elongated configuration extending along the delivery device lumen when the scaffold is in the collapsed configuration and a flexed configuration bowed away from the rigid element sufficiently when the scaffold is in the expanded delivery configuration to anchor the tissue traction system in place. In some embodiments, the scaffold includes a wire structure resilient to expand from a folded configuration when the scaffold is in the collapsed delivery configuration to a resiliently expanded configuration when the scaffold is in the deployed configuration to contact the tissue to anchor the tissue traction system in place. In some embodiments, the tissue traction element is pivotably coupled to the scaffold.

In yet another aspect, in accordance with various principles of the present disclosure a method of exerting traction on a region of a target tissue includes delivering a scaffold in a collapsed configuration to the target tissue; deploying the scaffold to allow the scaffold to expand to anchor the scaffold to tissue surrounding the target tissue; grasping a tissue traction element coupled to the scaffold; and pulling the tissue traction element towards the region of target tissue and coupling a portion of the tissue traction element to the region of target tissue to exert traction force on the grasped region of target tissue; where the tissue traction element is anchored in place with respect to the target tissue by the engagement of the scaffold with the tissue surrounding the target tissue without further action required to anchor the tissue traction device with respect to the tissue.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in factors of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows:

FIG. 4 is an elevational view of a tissue traction device similar to the devices illustrated in FIGS. 1-3, in a delivery configuration.

FIG. 5 is an exploded view of a tissue traction device as in FIG. 4.

DETAILED DESCRIPTION

Figure 1:
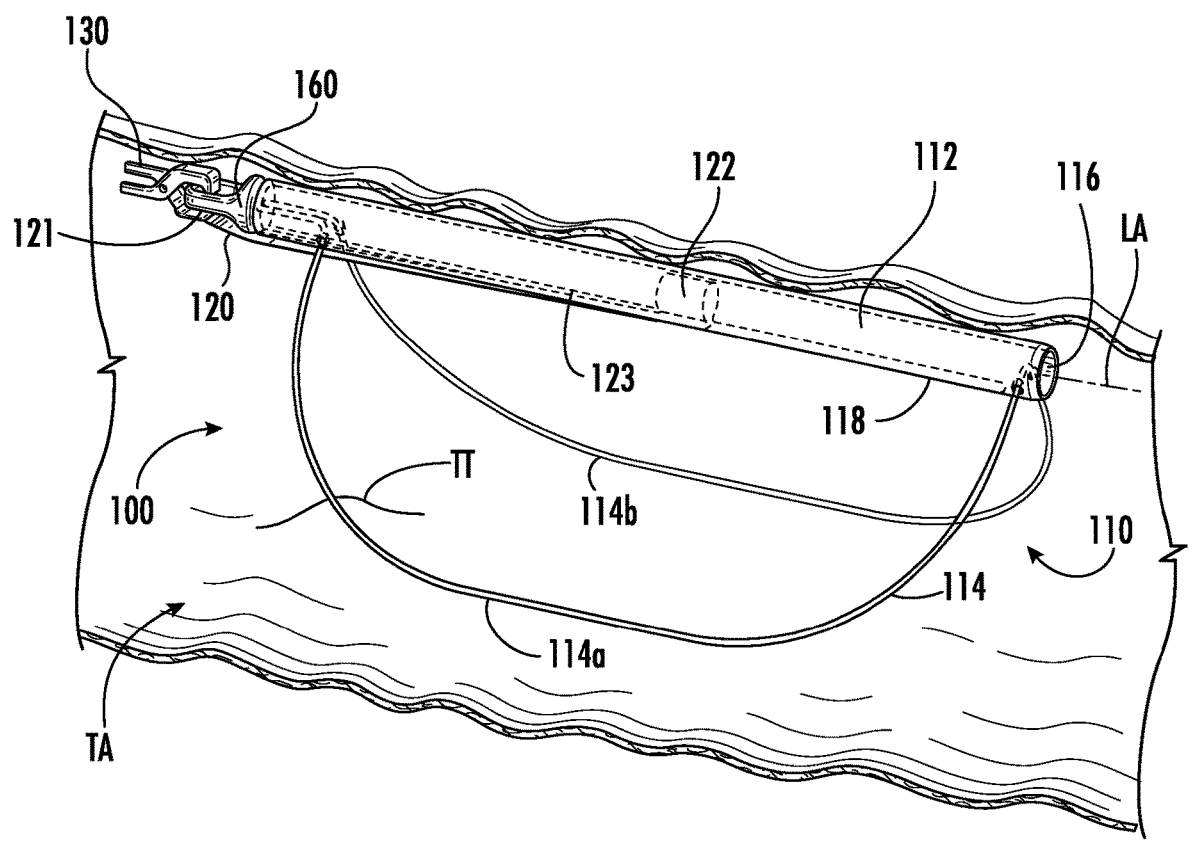
FIG. 1 is a perspective view of a tissue traction device in accordance with various aspects of the present disclosure, illustrated in a deployed configuration positioned in a schematic representation of a body lumen.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably without intent to limit or otherwise), etc., such as when using a device (e.g., introducing the device into a patient, or during implantation, positioning, or delivery), and "distal" refers to the direction or location furthest from the user, such as when using the device (e.g., introducing the device into a patient, or during implantation, positioning, or delivery). "Longitudinal" means extending along the longer or larger dimension of an element. "Central" means at least generally bisecting a center point, and a "central axis" means, with respect to an opening, a line that at least generally bisects a center point of the opening, extending longitudinally along the length of the opening when the opening comprises, for example, a tubular element, a strut, a channel, a cavity, or a bore.

A tissue traction element may be used to lift tissue away from a target tissue area at which a procedure is being performed. As used herein, the term "target tissue" is used herein to refer to an area or region of tissue on which a procedure is to be performed. In some instances, the target tissue is an unhealthy, diseased (i.e., cancerous, pre-cancerous etc.), or otherwise undesirable portion of tissue that may be healthy or unhealthy. A "target tissue" may also include tissues that are suspected of being unhealthy or diseased, but which require surgical removal for verification of their disease status by biopsy. It should be appreciated that surgical dissection of a "target tissue" typically includes removal of a portion of the surrounding healthy tissue along the "target tissue" margin to ensure complete removal and minimize the potential for metastasis of left behind or dislodged "target tissue" cells to other body locations. The target tissue is within a target tissue area at a treatment site in the body, such as the gastrointestinal system. The terms "target tissue area" or "target area of tissue" may be used interchangeably herein to refer to an area of tissue extending outwardly from or around or surrounding the target tissue.

The tissue traction element generally is coupled at a first location (along the tissue traction element) to a region (e.g., a portion) of the target tissue, and anchored at a second location (along the tissue traction element) to be stationary with respect to the target tissue. It will be appreciated that terms such as coupled, anchored, grasped, fixed, secured, attached, connected, etc. (and conjugations thereof) may be used interchangeably herein without intent to limit unless otherwise specifically indicated. The tissue traction element may coupled to the target tissue via another element such as a tissue engagement member configured to grasp both a portion of the tissue traction element as well as a portion of the target tissue. The tissue traction element is configured to actively lift or retract tissue to which it is coupled. For instance, the tissue traction element may be elastic and exert a force (e.g., traction force) on the grasped tissue. In the case of an elongated tissue traction element, the first location may be at the first end of the tissue traction element, and the second location may be at the second end of the tissue traction element. If the tissue traction element is not elongated, then the first and second locations preferably are spaced apart from one another sufficiently to allow the desired amount of traction to be applied to the tissue to be lifted.

In accordance with various principles of the present disclosure, unlike prior tissue traction devices or systems, a tissue traction element is anchored to a support structure such as a scaffold rather than to tissue spaced apart from the target tissue. In some embodiments, the scaffold structure is self-standing or self-supporting once deployed. In other words, the scaffold structure may be delivered, such as by a delivery device (e.g., a tubular element, such as a flexible elongate member having a lumen defined therein), and released from the delivery device to provide sufficient anchoring structure for the tissue traction element without addition of further structural support elements. The scaffold structure may include one or more components sized, shaped, structured, and configured to engage or contact (such terms being used interchangeably herein without intent to limit) tissue wall in the target tissue area to anchor or seat (such terms being used interchangeably herein without intent to limit) the tissue traction device with respect to the tissue wall. The scaffold structure may engage opposed regions of the tissue wall or regions sufficiently spaced apart to allow anchoring of the tissue traction device therebetween as a result of the contact of the scaffold with the tissue wall and without grasping or otherwise embedding into the tissue wall. For the sake of convenience and without intent to limit, reference will be made to opposed regions of the tissue wall, such reference intended to include reference to regions of the tissue wall that are not necessarily opposed from each other, but which are spaced apart from each other and positioned such that the scaffold may be seated therebetween to anchor the tissue traction device with respect to the tissue. As used herein, terms such as anchor or secure or the like are to be understood as little to no movement of the anchored structure relative to the tissue (or other element to which the anchored structure is anchored). In some embodiments, the scaffold shifts from a collapsed delivery configuration to an expanded deployed configuration when delivered to the target tissue area. The scaffold structure is shaped, sized, and configured based on the delivery site (target tissue area) such that expansion of the scaffold against the tissue wall exerts sufficient force to anchor the scaffold and the tissue traction device in place with respect to the target tissue area. Accordingly, it will be appreciated that upon expansion of the scaffold, additional steps to anchor the scaffold need not be taken to anchor the scaffold and tissue traction device in place. In further embodiments, the scaffold may be shifted from the deployed expanded configuration back to the collapsed delivery configuration to be retracted into the delivery device for removal from the target tissue area.

In some embodiments, the tissue traction element may be in the form of a traction band, with any desired cross-sectional shape (circular, oval, square, rectangular, etc.) or loop. The tissue traction element may have a degree of resiliency and expandability such that once stretched, the tissue traction element is biased to retract to its initial unstretched configuration. In some embodiments, the scaffold includes a flexible elongated wire frame and a rigid element. In some embodiments, the rigid element is elongated and the wire frame is flexible from an elongated configuration, extending along the longitudinal axis of the rigid element, to a bowed or flexed configuration expanded away from the rigid element. The tissue traction element may be coupled to the rigid element and extend therefrom to be coupled to target tissue to be lifted. In other embodiments, the wire frame is expandable from a collapsed configuration, such as in a confined position within the delivery device, to an expanded configuration when released from the delivery device. In such embodiment, the wire frame may be formed from a shape memory material to expand to a desired expanded configuration. The rigid element of such embodiment may have a first end pivotably coupled to the wire frame, with the tissue traction element coupled to the second end of the rigid element and extendable therefrom to be coupled to tissue to be lifted. In some embodiments, a biasing element, such as a torsional spring, acts on the rigid element to create a dynamic traction force in conjunction with the elastic tissue traction element (which may provide a more linear traction force).

In accordance with various principles of the present disclosure, the scaffold is configured such that when it is in the expanded configuration, the scaffold is sized to contact tissue walls in the region of the target tissue area to fit securely along the target tissue area. The expanded scaffold, when contacting the tissue walls, thereby remains in place (does not shift or otherwise move) relative to the target tissue area. In embodiments with a wire frame which bows from an elongated rigid element, the elongated rigid element may contact and anchor the scaffold with respect to a tissue wall. The wire frame may extend away from the elongated rigid element to contact another location along the tissue wall to anchor the scaffold in place. In embodiments with an expandable wire frame, different portions of the wire frame may contact different portions of the tissue wall to anchor the scaffold with respect to the tissue wall.

It will be appreciated that tissue traction devices formed in accordance with various principles of the present disclosure may be positioned with a body lumen (e.g., intestines) or within an organ (e.g., stomach) presenting tissue walls forming an environment (lumen or cavity or other shape with the tissue wall curving to form a space therebetween) in which the scaffold may be seated and anchored against. As noted above, the tissue walls need not be opposite one another, but should at least provide a sufficiently enclosed area with walls against which a portion of the tissue traction device may be securely positioned so as not to shift or move.

Various embodiments of tissue traction devices and systems and methods of use thereof will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present invention is not limited to only the embodiments specifically described herein.

It will be appreciated that in the following description, elements or components similar among the various illustrated embodiments are generally designated with the same reference numbers increased by a multiple of 100 and redundant description is omitted. Common features are identified by common reference elements and, for the sake of brevity, the descriptions of the common features are generally not repeated. For purposes of clarity, not all components having the same reference number are numbered.

Turning now to the drawings, an example of a tissue traction device 100 embodying various aspects of the present disclosure is illustrated in FIG. 1 in an expanded deployed configuration. The tissue traction device 100 is configured and sized for placement between opposed regions of a tissue wall (or regions sufficiently spaced apart to allow anchoring of the tissue traction device 100 therebetween) in a target tissue area TA to be anchored with respect to the tissue wall.

In accordance with various principles of the present disclosure, the tissue traction device 100 includes a scaffold structure 110 (which may be referenced herein as simply a scaffold 110 for the sake of convenience and without intent to limit) and a tissue traction element 120 coupled to the scaffold structure 110. The scaffold 110 is sized, shaped, structured, and configured to hold the tissue traction device 100 with respect to the tissue walls. The tissue traction element 120 is coupled to the scaffold 110 and is configured to be coupled to a portion or region of target tissue TT in the target tissue area TA to exert a traction force on such portion or region of the target tissue TT. It will be appreciated that the terms portion, region, and the like may be used interchangeably herein without intent to limit. In some embodiments, the tissue traction element 120 is an elastic element (e.g., made of elastomeric material), such as a band, a loop, or other configuration which may apply the desired amount of force to the target tissue TT. In some embodiments, a tissue engagement member 130 is coupled to a portion of the tissue traction element 120 (in the case of an elongated tissue traction element 120, such as illustrated, a free end 121 of the tissue traction element 120 unattached to another element or structure). The tissue engagement member 130 may be used to couple the tissue traction element 120 to a portion of the target tissue TT. The tissue traction element 120 may initially be positioned adjacent a portion of the scaffold 110, when the scaffold 110 is anchored against the tissue wall, as illustrated in FIG. 1.

Figure 2:
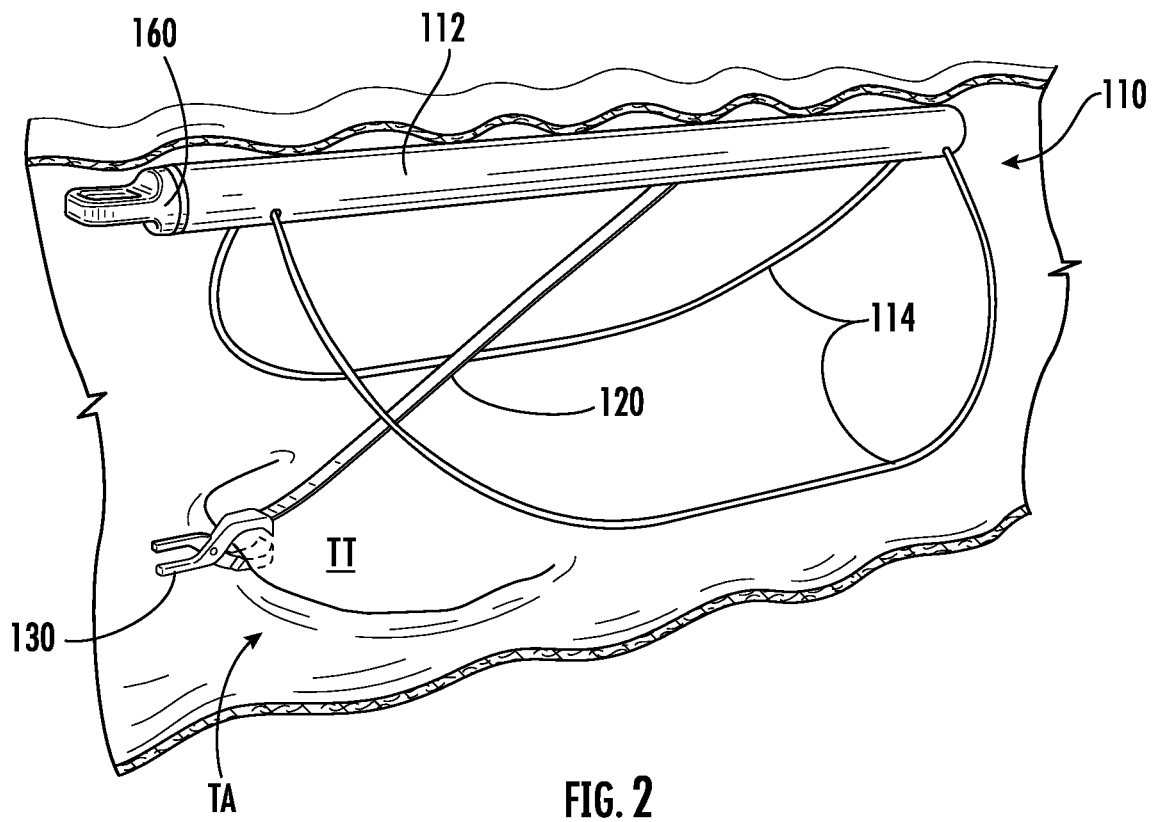
FIG. 2 is a perspective view of a tissue traction device similar to the device illustrated in FIG. 1, but with the tissue traction element extended to grasp tissue.

In embodiments in which the target tissue TT is cut, the tissue traction element 120 is coupled to a portion of the target tissue TT which is to be lifted or retracted or otherwise moved away from surrounding tissue at the target tissue area TA. The tissue engagement member 130, with the free end 121 of the tissue traction element 120 coupled thereto, may be extended away from the scaffold 110 to the target tissue area TA to grasp a portion of the target tissue TT, as illustrated in FIG. 2. To assist the tissue engagement member 130 with grasping the target tissue TT, the target tissue TT may be injected with saline to raise it somewhat with respect to the surrounding tissue. The tissue traction element 120 may be placed in tension when the tissue engagement member 130 is coupled to the target tissue TT. As such, when the target tissue area TA is cut around the grasped portion of the target tissue TT (such as with a cutting instrument 140), the tensioned tissue traction element 120 exerts a traction force on the grasped tissue and lifts the tissue away from surrounding tissue as it is cut, as illustrated in FIG. 3.

Figure 3:
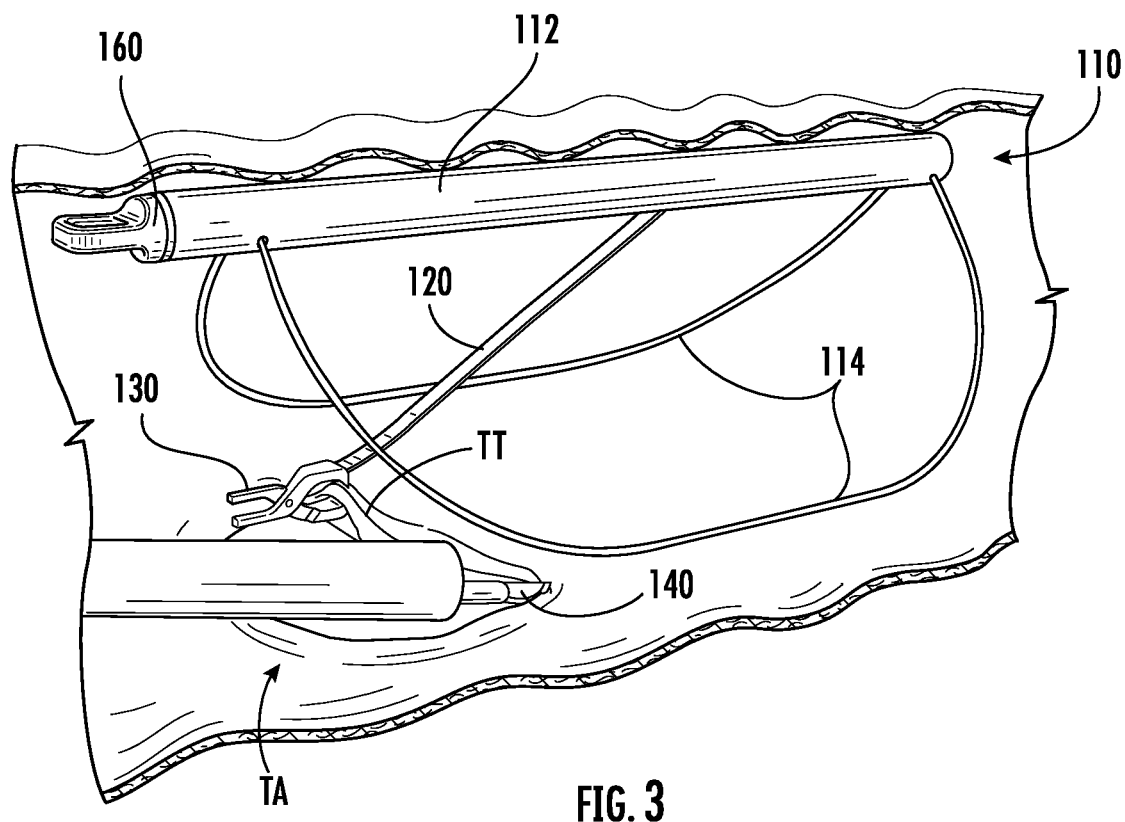
FIG. 3 is a perspective view of a tissue traction device similar to the device illustrated in FIG. 1 and FIG. 2, but with the grasped tissue being cut and the tissue traction element lifting the cut grasped tissue away from the cutting area.

In accordance with some aspects of the present disclosure, the embodiment of a scaffold 110 illustrated in FIGS. 1-3 includes a substantially rigid element 112 and an expandable wire structure 114. The rigid element 112 may be seated (e.g., anchored, placed, etc., such terms being used interchangeably herein without intent to limit) against a first area of tissue in the area of the target tissue area TA, and the wire structure 114 may be seated against a second area of tissue in the area of the target tissue area TA such that the scaffold 110 is anchored with respect to the tissue so as not to move relative to the target tissue TT even as the tissue traction element 120 applies traction force to the target tissue TT. Moreover, it will be appreciated that the wire structure 114 has sufficient rigidity to anchor the scaffold 110 in place against the tissue wall once deployed. Preferably, the scaffold 110 is anchored upon deployment without further assistance of another element (e.g., a tissue clip or anchor) and without further adjustment. The rigid element 112 may be formed of a biocompatible polymer (e.g., plastic) or metal sufficiently rigid to anchor the scaffold 110 in place and to withstand forces exerted by the tissue traction element 120. The wire structure 114 may be made of any suitable biocompatible metal such as nitinol or other super elastic material such as an ultra-high strength alloy.

As illustrated in FIG. 1, the rigid element 112 may have a lumen 116 defined therein in which an anchor end 123 of the tissue traction element 120 may be positioned (e.g., held or anchored or fixed, such terms being used interchangeably herein without intent to limit). In some embodiments, an anchor element 122 is provided on the anchor end 123 of the tissue traction element 120 to anchor the anchor end 123 with respect to the scaffold 110. In some embodiments, the anchor end 123 is substantially immovably anchored within the lumen 116 (such as by a friction fit of the anchor element 122 within the lumen 116, or by the use of adhesion or welding of the anchor element 122 within the lumen 116). When the free end 121 of the tissue traction element 120 is extended away from the scaffold 110 to grasp a portion of tissue, the tissue traction element 120 may extend from the anchor end 123 within the lumen 116 of the rigid element 112 through an elongated opening, such as a slit 118, defined along (e.g., longitudinally along) the wall of the rigid element 112. As the target tissue TT is cut, the tissue traction element 120 exerts a force on the grasped portion of tissue to lift or retract such portion of tissue away from the target tissue area TA. As such, a cut tissue flap does not interfere with the procedure being performed, with no actions beyond simply deploying the tissue traction device 100 and coupling the free end 121 of the tissue traction element 120 to a region of the target tissue TT.

In accordance with one aspect of the present disclosure, an embodiment of a tissue traction device 100 as illustrated in FIG. 1 is shiftable between a collapsed delivery configuration (such as illustrated in FIG. 4) and an expanded deployed configuration (such as illustrated in FIGS. 1-3) upon deployment, without further actions to deploy the tissue traction device 100. As such, anchoring of a tissue traction element 120 requires fewer steps and instruments than required by prior procedures. Delivery of the tissue traction device 100, in a collapsed delivery configuration (such as within a delivery device 150), to the target tissue area TA, and deployment thereof into the expanded deployed configuration, and use in the deployed configuration will now be described with reference to FIGS. 4-6.

In the collapsed delivery configuration illustrated in FIG. 4, the tissue traction device 100 is contracted or collapsed to fit within a lumen 152 defined within a delivery device 150. The delivery device 150 may be a flexible elongate member such as a catheter, sheath, tubular element, endoscope, etc. configured to navigate through the patient's body to carry and deliver the tissue traction device 100 to the target tissue area TA. The delivery device 150 may extend through a working channel of an endoscope or other further delivery device known or heretofore known in the medical field and not illustrated (for the sake of simplicity).

As may be appreciated with reference to FIG. 4 and the exploded view of the tissue traction device 100 illustrated in FIG. 5, the wire structure 114 is extended proximally, at least partially out of the proximal end 111 of the rigid element 112. As such, the wire structure 114 is substantially straight, or at least not bent or bowed greater than the diameter of the delivery device lumen 152, and thus the illustrated tissue traction device 100 may be considered to be in a compact delivery configuration. A proximal end 115 of the wire structure 114 may be coupled to a link 160. In some embodiments, the tissue engagement member 130 may be coupled to and/or carried by the link 160, such as being coupled to a proximal end 161 of the link 160. A distal end 117 of the wire structure 114 may be coupled to the rigid element 112, such as at or near a distal end 113 of the rigid element 112, so as not to become inadvertently detached therefrom.

A tissue engagement member 130 may be coupled to the proximal end 121 of the tissue traction element 120. At least an anchor end 123 of the tissue traction element 120 may be positioned within the lumen 116 of the rigid element 112. If a tissue engagement member 130 is provided, and coupled to a link 160 coupled to the proximal end 115 of the wire structure 114, then the proximal end 121 of the tissue traction element 120 extends proximally out of the proximal end 111 of the rigid element 112.

In some embodiments, the wire structure 114 has first and second legs 114a, 114b which are spaced apart to support the wire structure 114 against a tissue wall, as illustrated in FIG. 1. The legs 114a, 114b of the wire structure 114 enter the open proximal end 111 of the rigid element 112, and each of the legs 114a, 114b extends out of the rigid element 112 through a respective proximal aperture 119p defined in the wall of the rigid element 112 adjacent the proximal end 111 of the rigid element 112. The legs 114a, 114b extend distally towards the distal end 113 of the rigid element 112. As may be appreciated with reference to FIGS. 4 and 5, the legs 114a, 114b are substantially straight or are otherwise configured to fit within the lumen 116 of the rigid element 112 when in the collapsed deployed configuration illustrated in FIG. 4. The wire structure 114 extends distally towards the distal end 113 of the rigid element 112, and each of the legs 114a, 114b extends through a respective distal apertures 119d defined in the wall of the rigid element 112 adjacent the distal end 113 of the rigid element 112. The distal ends 117a, 117b of the legs 114a, 114b may be anchored to the wall of the rigid element 112, such as to retain the wire structure 114 and the rigid element 112 together. In some embodiments, the wire structure 114 is in the form of an open loop with the distal ends 117a, 117b of the legs 114a, 114b forming the closed distal end 117 of the loop within the lumen 116 of the rigid element 112, and the free, unattached ends of the legs 114a, 114b extending proximally. If a link 160 is provided, the proximal ends 115a, 115b of the legs 114a, 114b may be coupled to the link 160. The apertures 119p, 119d may be positioned about the circumference of the rigid element 112 to maintain the legs 114a, 114b spaced from each other to provide sufficient anchoring stability to the tissue traction device 100 once deployed.

Figure 6:
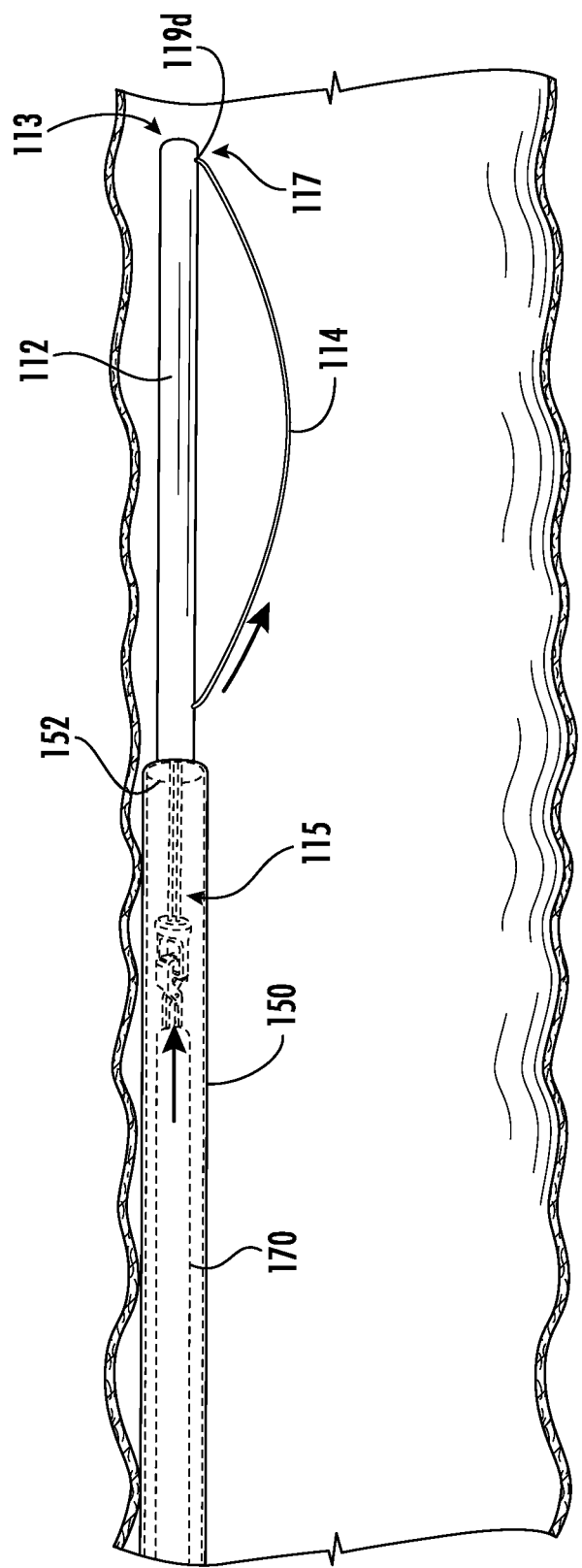
FIG. 6 is an elevational view of a tissue traction device as in FIGS. 4 and 5 being shifted into a deployed configuration.

The rigid element 112 may thus act as a supporting part in routing the wire structure 114 through the delivery device 150. The tissue traction device 100 may be pushed distally out of the delivery device 150 by a pusher 170 (e.g., a push rod or push wire or other device capable of pushing the tissue traction device 100 as known or heretofore known in the art). In some embodiments, the pusher 170 may push the tissue traction device 100 via the tissue engagement member 130 and/or the link 160. As illustrated in FIG. 6, the rigid element 112 is advanced distally up to a point at which only a proximal section of the rigid element 112 adjacent the proximal end 111 thereof remains within the delivery device 150. The pusher 170 continues to distally advance the wire structure 114, with the proximal end 111 of the rigid element 112 remaining within the lumen 152 of the delivery device 150. Because the wire structure 114 is no longer constrained by the walls of the walls of the delivery device lumen 152, the wire structure 114 bows or flexes or bends (such terms being used interchangeably herein without intent to limit) outwardly away from the rigid element 112, as illustrated in FIG. 6, with continued distal advancement of the wire structure 114. In embodiments with a link 160, the link 160 (e.g., a distal end 163 of the link 160, as may be seen in FIG. 5) is secured in place within the lumen 116 of the rigid element 112 and the wire structure 114 is thereby retained in its bowed configuration, as illustrated in FIG. 1.

The size, shape, flexibility/rigidity, and configuration of the tissue traction device 100, particularly the wire structure 114 thereof, are selected to fit in the target tissue area TA to anchor the tissue traction device 100 in place. For instance, the degree of bowing of the wire structure 114 and the distance between the portion of the wire structure 114 furthest from the rigid element 112 are selected to be slightly greater than the distance between opposing walls in the region of the target tissue area TA so that the rigid element 112 and the wire structure 114 may be secured in position against the tissue walls to anchor the tissue traction device 100 in place.

Once the scaffold 110 has been pushed out of the delivery device 150 to be deployed and anchored in place, the tissue traction element 120 may be coupled to a region of the target tissue TT, such as with a tissue engagement member 130 in any known or heretofore known manner. For instance, in the embodiment illustrated in FIGS. 1-6, a tissue engagement member 130 coupled to the tissue traction element 120 and a link 160 may be disengaged from the link 160 to grasp target tissue TT and to couple the tissue traction element 120 to the grasped tissue, as illustrated in FIG. 2 and FIG. 3. If the tissue traction element 120 is coupled to an anchor element 122 within the rigid element 112, then tissue traction element 120 is extended therefrom through the slit 118 in the wall of the rigid element 112 by the tissue engagement member 130. As may be appreciated upon comparison of FIG. 2 and FIG. 3, as tissue at the target tissue area TA is cut by an instrument 140, the tissue grasped by the tissue engagement member 130 is lifted by the tension of the tissue traction element 120. As such, the medical professional need not be concerned with moving the cut flap or region of tissue out of the way to view the target tissue area TA on which the procedure is being performed.

When the tissue traction device 100 is no longer needed, the tissue traction device 100 may be retracted proximally, such as into the same delivery device 150 or another tubular device with a lumen which may constrain the tissue traction device 100 into a collapsed configuration, for removal from the target tissue area TA. In an embodiment with a link 160, the link 160 may be pulled proximally out of the proximal end 111 of the rigid element 112, pulling the wire structure 114 proximally to move from the bowed configuration to an elongated configuration which may fit into a delivery device in which the tissue traction device 100 is to be removed.

It will be appreciated that various modifications to a tissue traction device formed in accordance with principles of the present disclosure are within the scope and spirit of the present disclosure. Tissue traction devices 200, 300 with a modified scaffold structure 210 and a modified tissue traction element 220 are illustrated in FIGS. 7-12.

As in the embodiment of a tissue traction device 100 illustrated in FIGS. 1-6, the scaffold structures 210, 310 of the embodiment of a tissue traction device 200, 300 illustrated in FIGS. 7-12 is sized, shaped, structured, and configured to hold the tissue traction device 200, 300 with respect to the tissue walls. Also as in the tissue traction device 100 illustrated in FIGS. 1-6, the tissue traction element 220, 320 of the tissue traction device 200, 300 of FIGS. 7-12 is coupled to a scaffold 210, 310 and is configured to be coupled to a portion of target tissue TT in the target tissue area TA by a tissue engagement member 230, 330 to exert a traction force on such portion of the target tissue TT. However, the tissue traction devices 200, 300 of FIGS. 7-12 have various modifications to the scaffold structure and/or the tissue traction element of the embodiment illustrated in FIGS. 1-6 without departing from the scope and spirit of the present disclosure, as will now be described with reference to the embodiment of a tissue traction device 200 illustrated in FIGS. 7-11. It will be appreciated that structures of the embodiment of the tissue traction device 300 illustrated in FIG. 12 which are similar to structures of the embodiment of the tissue traction device 200 illustrated in FIGS. 7-11 are referenced with similar reference numerals increased by 100. For the sake of brevity, description of similar structures is not repeated.

In contrast with the wire structure 114 of the embodiment of FIGS. 1-6, which anchors the scaffold 110 in cooperation with a rigid element 112 (with the wire structure 114 seated against one portion of the tissue wall and the rigid element 112 seated against an opposed portion of the tissue wall), the wire structure 214 of the scaffold 210 of the embodiment of FIGS. 7-12 seats against opposing tissue walls to anchor the tissue traction device 200 in place without cooperation of a rigid element. More particularly, the wire structure 214 of the tissue traction device 200 illustrated in FIGS. 7-12 is sized, shaped, structured, and configured to extend across the opposed tissue walls to contact both opposed walls to hold the tissue traction device 200 in place. In the illustrated example of an embodiment, the scaffold 210 has first and second legs 214a, 214b spaced apart to support the wire structure 214 against a tissue wall. Additionally, the scaffold 210 has opposed first and second wire structure sections 214c, 214d, each configured to anchor the tissue traction device 200 by being seated against opposing portions of the tissue wall in the region of the target tissue area TA. As may be appreciated with reference to the example of an embodiment of a scaffold 210 illustrated in FIGS. 7-10, a scaffold 210 may include a first wire structure section 214c seated against a first region of a tissue wall in a target tissue area TA, and a second wire structure section 214d seated against a second region of the tissue wall opposite or sufficiently spaced apart from the first region of the tissue wall to allow the wire structure 214 to be anchored with respect to the tissue wall. The wire structure legs 214a, 214b are spaced apart with the target tissue TT positioned therebetween. The wire structure 214 may have a bend section 214e between (and coupling) the first and second wire structure sections 214a, 214b. In some embodiments, at least the bend section 214e of the wire structure 214 is formed to bias apart the first and second sections 214c, 214d of the wire structure 214 into the deployed configuration illustrated in FIGS. 7, 9, and 10. The wire structure 214, or at least the bend section 214e, may be formed of a shape memory material or other resiliently biased structure or material which exerts a force separating the first and second sections 214c, 214d of the wire structure 214 to anchor the first and second sections 214c, 214d against opposed regions of the tissue wall against which the tissue traction device 200 is to be anchored.

Additionally, or alternatively, in contrast with the tissue traction device 100 of the embodiment of FIGS. 1-6, the embodiment of a tissue traction device 200 illustrated in FIGS. 7-11 has a rigid element 212 which does not contribute to the anchoring provided by the scaffold 210 thereof. As with the rigid element 112 of the tissue traction device 100 illustrated in FIGS. 1-6, a tissue traction element 220 is coupled to the rigid element 212 of the tissue traction device 200 illustrated in FIGS. 7-11. However, unlike the rigid element 112 illustrated in FIGS. 1-6, the rigid element 212 of the tissue traction device 200 illustrated in FIGS. 7-11 is pivotably coupled to the wire structure 214. As such, the tissue traction element 220 is pivotably coupled to the wire structure 214 as well. The tissue traction element 220 is substantially fixedly coupled to a first end 211 of the rigid element 212 or may extend within a lumen within the rigid element 212 and coupled/fixed therein. The free end 221 (extending away from and not coupled to the rigid element 212) is graspable by a tissue engagement member 230.

Although the free end 221 of the tissue traction element 220 is illustrated in FIGS. 7-11 has having a loop shape (integrally formed with the elongated section 224 of the tissue traction element 220, or separately formed and coupled thereto), other configurations are within the scope and spirit of the present disclosure. For instance, instead of the tissue traction element 220 being substantially elongated, the tissue traction element 220 may be formed of one or more loops linked together, or other configurations suitable for grasping by a tissue engagement member 230. The second end 213 of the rigid element 212 may be formed with a pivot connection 218 by which the rigid element 212 is pivotably coupled to the wire structure 214, such as an aperture through which a portion of the wire structure 214 extends. In some embodiments, a biasing element 262, such as a spring (e.g., a torsion spring), biases the rigid element 212, and thus the tissue traction element 220 coupled thereto, distally away from the distal end 217 of the wire structure 214 such as to enhance traction force which may be applied by the tissue traction element 220, as will be described in further detail below.

Figure 7:
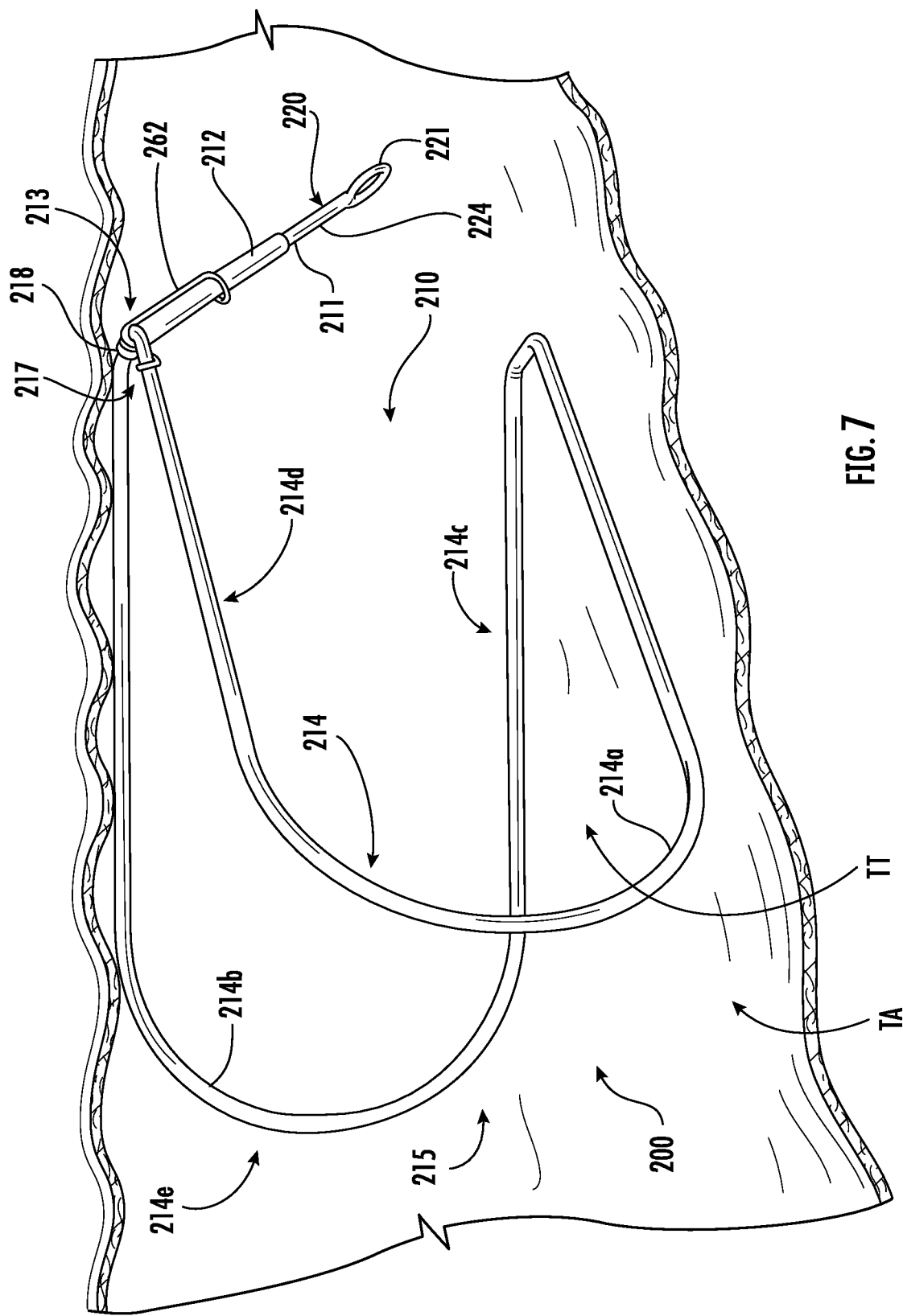
FIG. 7 is a perspective view of a tissue traction device in accordance with various aspects of the present disclosure, illustrated in a deployed configuration positioned in a schematic representation of a body lumen.
Figure 8:
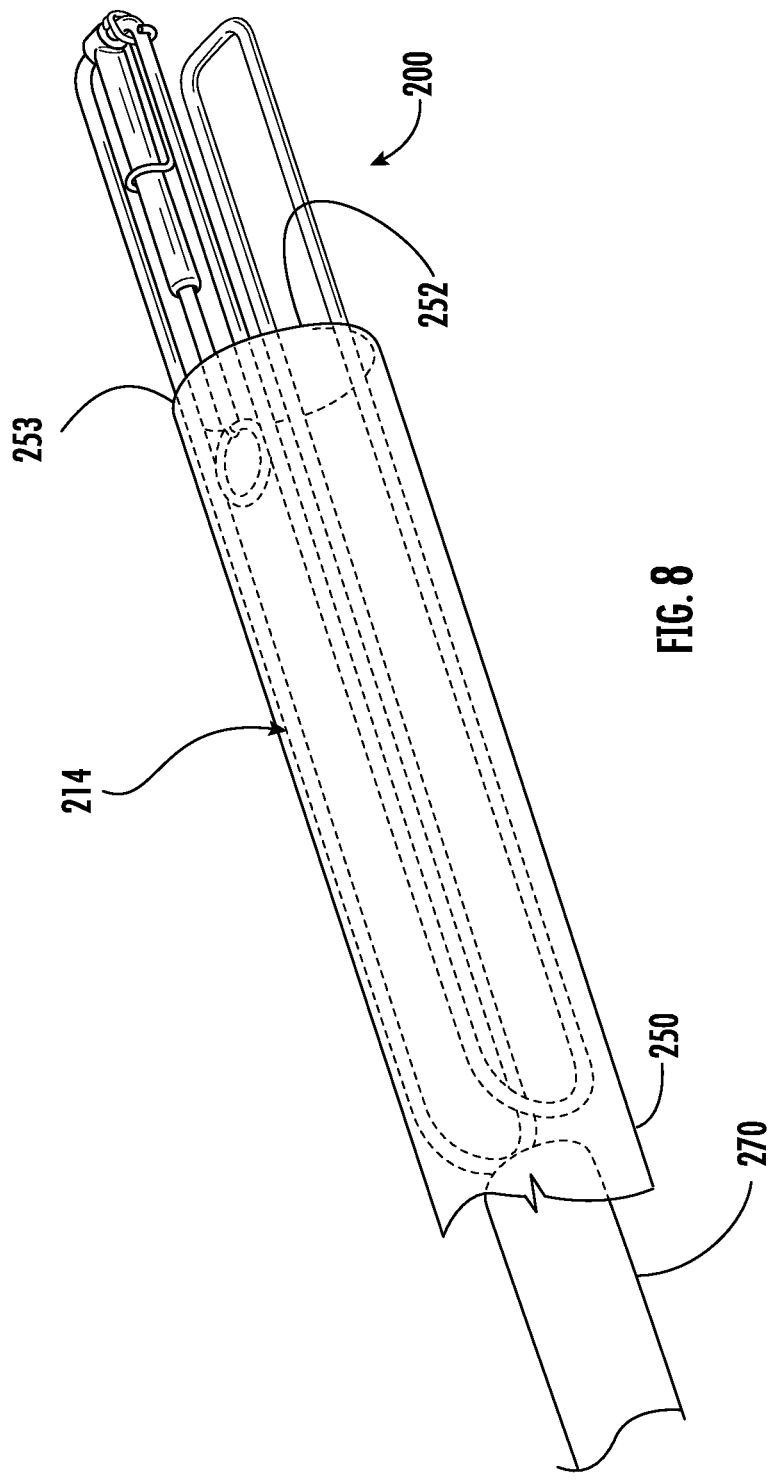
FIG. 8 is a perspective view of a tissue traction device similar to the devices illustrated in FIG. 7, in a delivery configuration.

Like the tissue traction device 100 illustrated in FIGS. 1-6, in accordance with one aspect of the present disclosure, an embodiment of a tissue traction device 200 as illustrated in FIG. 7 is shiftable between a collapsed delivery configuration (such as illustrated in FIG. 8) and an expanded deployed configuration (such as illustrated in FIGS. 7 and 9-11). Delivery of the tissue traction device 200, in a collapsed delivery configuration (such as within a delivery device 250), to the target tissue area TA, and deployment thereof into the expanded deployed configuration, and use in the deployed configuration will now be described with reference to FIGS. 8-11.

In the collapsed delivery configuration illustrated in FIG. 8, the tissue traction device 200 is contracted or collapsed to fit within a lumen 252 defined within a delivery device 250. The delivery device 250 may be a flexible elongate member such as a catheter, sheath, tubular element, endoscope, etc. configured to navigate through the patient's body (e.g., via an endoscope) to carry and deliver the tissue traction device 200 to the target tissue area TA. As illustrated in FIG. 8, the wire structure 214 is collapsible or foldable to fit within the lumen 252 of the delivery device 250. For instance, the wire structure 214 is folded along the bend section 214e to bring the first and second sections 214c, 214d of the wire structure 214 closer together to place the wire structure 214 in a compact configuration which may fit within the lumen 252 of the delivery device 250. The rigid element 212 is pivoted with respect to the wire structure 214 to extend along the lumen 252 of the delivery device 250. The rigid element 212 may be positioned extending proximally towards the proximal end 215 of the wire structure 214 (in a space between the wire structure legs 214a, 214b), as illustrated in FIG. 8, or may extend distally away from the wire structure 214, yet substantially aligned with the lumen 252 of the delivery device 250.

The tissue traction device 200 may be pushed distally by a pusher 270 (e.g., a push rod or push wire or other device capable of pushing the tissue traction device 200 as known or heretofore known in the art) to exit out the open distal end 253 of the delivery device 250. When the tissue traction device 200 is no longer restrained by the delivery device 250, the first and second sections 214c, 214d of the wire structure 214 expand away from each other (such as in response to a biasing force exerted by the bend section 214e) to be seated against opposed tissue walls, as illustrated in FIG. 7 and as described above. The free end 221 of the tissue traction element 220 is thereby deployed for engagement and coupling with a region of target tissue TT without further action beyond pushing the tissue traction device 200 out of the delivery device 250.

Figure 9:
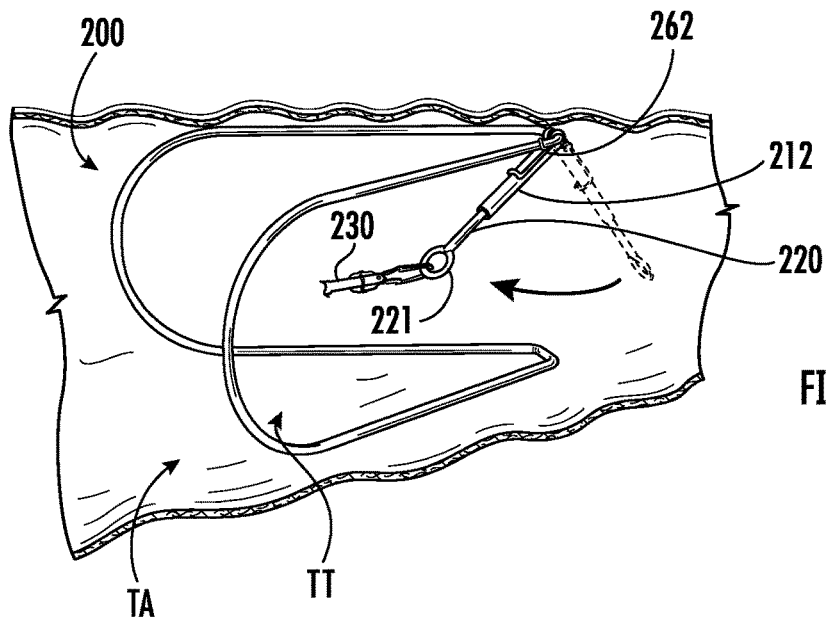
FIG. 9 is a perspective view of a tissue traction device similar to the devices illustrated in FIGS. 7 and 8, but with the rigid element and tissue traction element being pivoted to grasp tissue.

A tissue engagement member 230 may be advanced to the tissue traction element 220 (e.g., through the same lumen 252 through which the tissue traction device 200 was advanced, or through a different working channel of an endoscope or other delivery device as know or heretofore known in the medical field) and coupled to the distal end 221 of the tissue traction element 220, as illustrated in FIG. 9. In some embodiments, the tissue engagement member 230 is configured (e.g., with jaws, as illustrated, though other configurations are within the scope and spirit of the present disclosure) to grasp the free end 221 of the tissue traction element 220 as well a region of target tissue TT. As the tissue engagement member 230 moves (e.g., pulls) the tissue traction element 220 towards the region of target tissue TT to be grasped, the rigid element 212 pivots with respect to the wire structure 214. If a biasing element 262 is provided between the wire structure 214 and the rigid element 212, the rigid element 212 and the tissue traction element 220 are moved against the bias of the biasing element 262.

Figure 10:
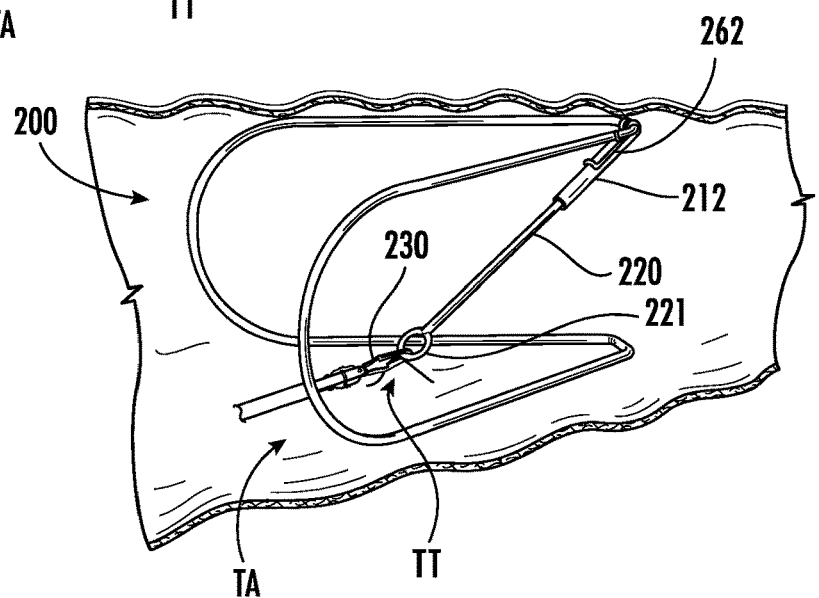
FIG. 10 is a perspective view of a tissue traction device similar to the devices illustrated in FIG. 7-9, but with the tissue traction element extended to grasp tissue.

As illustrated in FIG. 10, the tissue engagement member 230 and the free end 221 of the tissue traction element 220 of the tissue traction device 200 are coupled to a region of target tissue TT. To assist the tissue engagement member 230 with grasping the target tissue TT, the target tissue TT may be injected with saline to raise it somewhat with respect to the surrounding tissue. In an embodiment in which the tissue traction element 220 is resilient, the tissue traction element 220 is stretched or expanded from a resting configuration (FIG. 9) to an extended configuration (FIG. 10) when coupled to the target tissue TT, at least initially (before further actions on the target tissue TT are performed at the target tissue area TA and/or on the target tissue TT). As such, the resiliency of the tissue traction element 220 applies a biasing or traction or retraction force (such terms may be used interchangeably herein without intent to limit) on the grasped region of target tissue TT. In addition, in an embodiment in which a biasing element 262 is provided, the rigid element 212 is moved against the biasing force of the biasing element 262. As such, the biasing element 262 applies a biasing force on the grasped region of target tissue TT in addition to the force generated by a resilient tissue traction element 220. The combination of traction applied by the tissue traction element 220 and the biasing element 262 provide dynamicity to the forces applied by the tissue traction device 200 by combining an elastic, substantially linear force with a torsional force.

Figure 11:
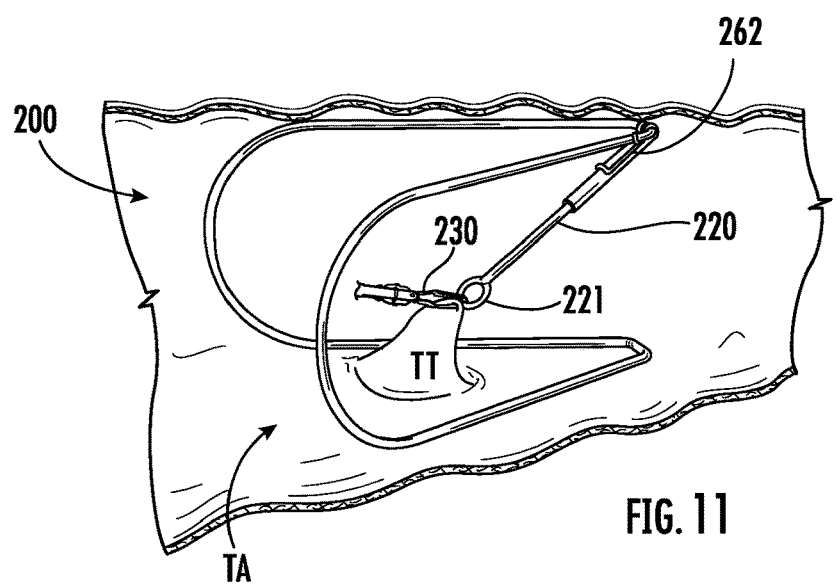
FIG. 11 is a perspective view of a tissue traction device similar to the device illustrated in FIG. 7-10, but with the tissue traction element being coupled to target tissue with a tissue engagement member.

The biasing forces generated in the tissue traction element 220 and/or by the biasing element 262 cause the tissue traction element 220 to pull on the tissue region to which the distal end 221 of the tissue traction element 220 is coupled (via the tissue engagement member 230), as illustrated in FIG. 11. Once the target tissue TT is cut around the grasped region of tissue, the grasped region of tissue is lifted by the tissue traction device 200 away from the surrounding areas of tissue in the target tissue area TA. As the grasped region of target tissue TT is lifted, the tissue traction element 220 may contract in length and may apply less tension to the tissue. The biasing force provided by the biasing element 262 counters such possible reduction in traction force by biasing (e.g., pivoting) the rigid element 212, and thus the tissue traction element 220, away from the target tissue area TA, thereby maintaining traction force on the grasped region of target tissue TT. Accordingly, the force (e.g., traction force) on the grasped region of target tissue TT will be maintained without falling beyond a minimum value to keep the grasped tissue lifted as desired. The force might vary, based on the state of the tissue traction element 220 and the position of the rigid element 212 and biasing element 262.

When the tissue traction device 200 is no longer needed, the tissue traction device 200 may be retracted proximally, such as into the same delivery device 250 or another tubular device with a lumen which may constrain the tissue traction device 200 into a collapsed configuration for removal from the target tissue area TA. The wire structure 214 may be sufficiently flexible such that proximal retraction of the bend section 214e thereof towards the lumen of the delivery device bends the wire structure 214 into the folded delivery configuration.

Figure 12:
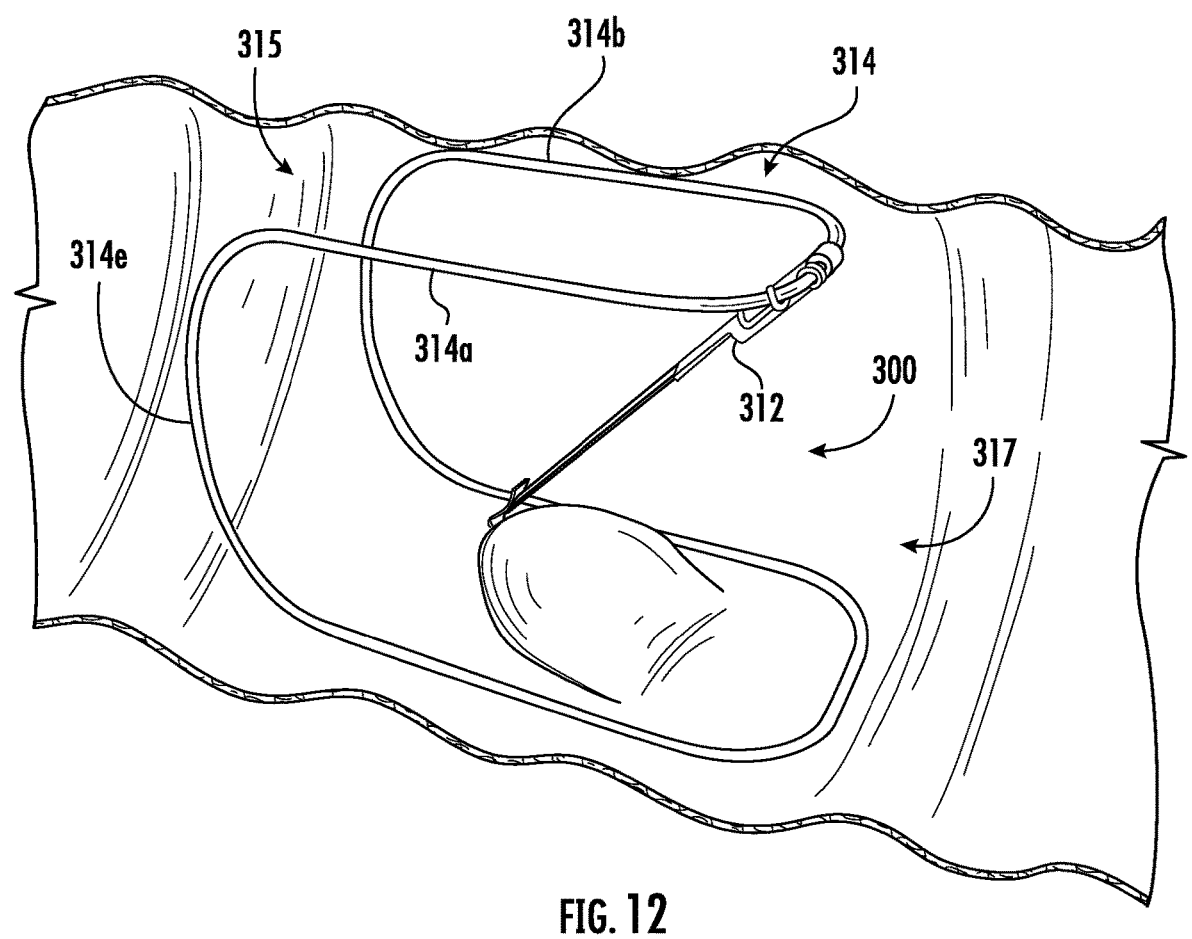
FIG. 12 is a perspective view of a modified tissue traction device similar to the devices illustrated in FIGS. 7-11 and in a deployed configuration.

As noted above, various modifications to a tissue traction device formed in accordance with principles of the present disclosure are within the scope and spirit of the present disclosure. Several modifications to a tissue traction device 200 such as illustrated in FIGS. 7-11 are illustrated with respect to an example of a tissue traction device 300 illustrated in FIG. 12. As in the tissue traction device 200 illustrated in FIGS. 7-11, the tissue traction device 300 has a scaffold structure 310 which includes a rigid element 312 and a wire structure 314. However, the shape of the wire structure 314 of the tissue traction device 300 illustrated in FIG. 12 may be somewhat different from that of the wire structure 214 of the tissue traction device 200 illustrated in FIGS. 7-12. Instead of the legs 214a, 214b of a wire structure 214 being spaced apart at a proximal end 215 and closer together at a distal end 217 thereof, the legs 314a, 314b of the wire structure 314 may be substantially uniformly spaced apart (e.g., extend parallel to each other) between the proximal end 315 and the distal end 317 of the wire structure 314, as illustrated in FIG. 12. It will be appreciated that the wire structure 314 preferably is sufficiently flexible at the distal end 317 (such as along a bend section 314e) thereof to allow the wire structure 314 to collapse or contract to a sufficiently compact size to fit within a lumen of a delivery device such as described above with respect to the tissue traction device 200 of FIGS. 7-11.

Alternatively or additionally, the rigid element 312 of the tissue traction device 300 may have a substantially flat cross-sectional shape, as illustrated in FIG. 12, in contrast with the substantially round cross-sectional shape illustrated in the tissue traction device 200 of FIGS. 7-11. It will be appreciated that other shapes and configurations of a rigid element are within the scope and spirit of the present disclosure.

In contrast with the example of a tissue traction element 220 illustrated in FIGS. 7-12, having a free end 221 configured to be grasped by a tissue engagement member 230, a tissue traction element 320 may be provided with a tissue engagement member 330 mounted and carried thereon, as illustrated in FIG. 12.

Various other structures of the tissue traction device 300 are substantially similar to similarly labeled structures (differing by 100) of the tissue traction device 200 illustrated in FIGS. 7-11 and thus such descriptions are not repeated. Moreover, the tissue traction device 300 illustrated in FIG. 12 may be deployed and removed in a similar manner as with the tissue traction device 200 illustrated in FIGS. 7-11, and therefore such description is not repeated.

It should be understood that one or more of the features described with reference to one embodiment can be combined with one or more of the features of any of the other embodiments provided herein. That is, any of the features described herein can be mixed and matched to create hybrid designs, and such hybrid designs are within the scope of the present disclosure.

The medical devices, instruments, tools, etc. to be used in conjunction with the present disclosure are not limited, and may include a variety of medical devices for accessing body passageways, including, for example, duodenoscopes, catheters, ureteroscopes, bronchoscopes, colonoscopes, arthroscopes, cystoscopes, hysteroscopes, and the like. A delivery device used herewith may be any suitable size, cross-sectional shape or area, and/or configuration permitting introduction and passage of medical devices, instruments, tools, etc. to the distal end of the delivery device. It is generally beneficial for the delivery device to be steerable, and the delivery device may have different areas of different flexibility or stiffness to promote steerability. A delivery device for a tissue traction device disclosed herein may be positioned in a further delivery device which may include one or more working channels extending substantially longitudinally (axially) between the proximal end and the distal end of the further delivery device. Delivery devices and/or overtubes associated therewith may be made from any suitable biocompatible material known to one of ordinary skill in the art and having sufficient flexibility to traverse non-straight or tortuous anatomy. Such materials include, but are not limited to, rubber, silicon, synthetic plastic, stainless steel, metal-polymer composite; metal alloys of nickel, titanium, copper cobalt, vanadium, chromium, and iron; superelastic or shape memory material such as nitinol (nickel-titanium alloy); different layers of different materials and reinforcements. Such materials may be made of or coated with a polymeric or lubricious material to enable or facilitate passage of a deliver device therethrough. In some embodiments, the working channels may be made of or coated with a polymeric or lubricious material to facilitate passage of the introduced medical instrument(s) through the working channel(s).

Various additional medical devices, instruments, tools, etc. may be used in conjunction with a tissue traction device formed in accordance with principles of the present disclosure. For instance, such instruments or tools may be used to perform a procedure or operation which is either diagnostic or therapeutic or both, such as grasping, resecting, dissecting, retracting, cutting, and/or otherwise manipulating tissue. Such instruments or tools include graspers (e.g., a rotatable grasping clip, with a pair of jaws/arms, etc.), cutting tool (e.g., knife, electrocautery device, scissors), snares, etc. A tissue engagement member contemplated for use with a tissue retraction device formed in accordance with principles of the present disclosure may include a naturally open/biased configuration configured to move to a closed/clamped configuration upon actuation by a handle assembly. Alternatively, a tissue engagement member contemplated for use with a tissue retraction device formed in accordance with principles of the present disclosure may include a naturally closed/biased configuration configured to move an open configuration upon actuation by a handle assembly.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The following claims are hereby incorporated into this Detailed Description by this reference, with each claim standing on its own as a separate embodiment of the present disclosure. Reference signs in the claims are provided merely as a clarifying example and shall not be construed as limiting the scope of the claims in any way.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "the", "first", "second", etc., do not preclude a plurality. Reference signs in the claims are provided merely as a clarifying example and shall not be construed as limiting the scope of the claims in any way.

What is claimed is:

1. A tissue traction device comprising:
a self-supporting scaffold having a proximal terminal free end and a distal terminal free end, and shiftable between a delivery configuration within a delivery device configured to deliver said tissue traction device to target tissue within a patient, and a deployed configuration released from the delivery device with the proximal terminal free end and the distal terminal free end outside of and separated apart from and independent of the delivery device and completely within the patient when deployed from the delivery device, and expandable to be anchored with respect to tissue surrounding a region of the target tissue within the patient; and
a tissue traction element having a first free end directly coupled to said scaffold, and a second end free configured to be coupled to the region of target tissue via a separately formed tissue engagement member;
wherein said self-supporting scaffold is sized, shaped, structured, and configured to be anchored with respect to the region of target tissue as said tissue traction element exerts a traction force on tissue.

2. The tissue traction device of claim 1, wherein said scaffold comprises a wire structure and a rigid element.

3. The tissue traction device of claim 2, wherein said wire structure is configured to bow away from said rigid element, said wire structure being configured to engage a first region of the tissue, and the rigid element being configured to engage a second region of the tissue spaced apart from the first region to anchor said tissue traction device with respect to the tissue.

4. The tissue traction device of claim 3, wherein said wire structure is movable with respect to said rigid element between an elongated configuration in which said tissue traction device is in a collapsed delivery configuration for fitting within a lumen of a delivery device, and a bowed configuration extending away from said rigid element when said tissue traction device is in an expanded deployed configuration separated from the delivery device.

5. The tissue traction device of claim 4, wherein:
said rigid element comprises a wall defining a lumen therein;
said wire structure extends through a proximal end of said rigid element into the lumen thereof, through a proximal aperture adjacent a proximal end of said rigid element wall, along a length of said rigid element, and through a distal aperture adjacent a distal end of said rigid element wall, said wire structure having a distal end secured within said lumen in said rigid element adjacent the distal end of said rigid element; and
said wire structure is shiftable from an elongated configuration extending along the rigid element and partially within the lumen of the rigid element, to a bowed configuration flexing away from said rigid element along a portion of said wire structure extending outwardly from said rigid element between the proximal aperture and the distal aperture in said rigid element wall.

6. The tissue traction device of claim 5, wherein said wire structure comprises first and second legs, each of said legs extending through the proximal end of said rigid element into the lumen thereof, through a respective proximal aperture in said rigid element wall, along a length of said rigid element, and through a respective distal aperture in said rigid element wall, said legs of said wire structure each having a distal end secured within said lumen in said rigid element adjacent the distal end of said rigid element.

7. The tissue traction device of claim 2, wherein said wire structure comprises a first section configured to engage a first region of the tissue and a second section configured to engage a second region of the tissue spaced apart from the first region, said first section and said second section biased apart to anchor said tissue traction device with respect to the tissue.

8. The tissue traction device of claim 7, wherein said rigid element is pivotably coupled to a distal end of said wire structure, and a biasing element biases said rigid element in a distal direction away from said wire structure.

9. The tissue traction device of claim 2, wherein said tissue traction element is elastic and pivotably coupled with respect to a portion of said scaffold.

10. The tissue traction device of claim 9, wherein said tissue traction element extends from said rigid element.

11. The tissue traction device of claim 10, wherein:
said rigid element is tubular and defines a lumen therein; and
the first end of said tissue traction element is coupled to said rigid element within the lumen defined in said rigid element.

12. The tissue traction device of claim 10, wherein:
the first end of said tissue traction element is coupled to a first end of said rigid element;
a second end of said rigid element is coupled to a distal end of said wire structure; and
a biasing element is positioned with respect to the second end of said rigid element and said wire structure to bias said rigid element and said tissue traction element in a distal direction away from said wire structure.

13. The tissue traction device of claim 1, wherein said scaffold in the delivery configuration is in a collapsed configuration sized to fit the proximal terminal free end and the distal terminal free end thereof within a lumen of a delivery device, and said scaffold in the deployed configuration is sized to engage the tissue to anchor the tissue traction device with respect to the tissue.

14. The tissue traction device of claim 13, wherein said scaffold shifts from a longitudinally extended delivery configuration to a flexed expanded deployed configuration.

15. The tissue traction device of claim 13, wherein said scaffold shifts from a folded delivery configuration to the expanded deployed configuration.

16. A tissue traction system comprising:
a delivery device defining a lumen therethrough;
a scaffold having a proximal terminal free end and a distal terminal free end, and configured to be anchored with respect to tissue within a patient surrounding a region of target tissue within the patient upon contact with the target tissue by shifting from a collapsed delivery configuration sized to fit within the delivery device lumen to an expanded deployed configuration with the proximal terminal free end and the distal terminal free end outside and deployed from the delivery device and completely within the patient, and with the scaffold configured and sized to engage the tissue to anchor the tissue traction device with respect to the tissue;
a separately formed tissue engagement member configured to grasp the region of target tissue; and
a tissue traction element having a first terminal end anchored to said scaffold, and a second end free to be coupled to the region of target tissue by said tissue engagement member to exert traction on the target tissue with said scaffold anchored with respect to tissue walls.

17. A tissue traction system as in claim 16, wherein said scaffold comprises a rigid element and a wire structure resilient to shift between an elongated configuration extending along the delivery device lumen when the scaffold is in the collapsed configuration, and a flexed configuration bowed away from said rigid element sufficiently when said scaffold is in the expanded delivery configuration, with the terminal free ends thereof completely within the patient, to anchor said tissue traction system in place.

18. A tissue traction system as in claim 16, wherein said scaffold comprises a wire structure resilient to expand from a folded configuration when said scaffold is in the collapsed delivery configuration to a resiliently expanded configuration when said scaffold is in the deployed configuration to contact the tissue to anchor said tissue traction system in place.

19. A tissue traction system as in claim 16, wherein said tissue traction element is pivotably coupled to said scaffold.

20. A method of exerting traction on a region of a target tissue within a patient,
said method comprising:
delivering a scaffold, having a proximal terminal free end and a distal terminal free end, in a collapsed configuration, within a delivery device, to the target tissue;
deploying the scaffold within the patient;
and releasing the scaffold from the delivery device to be separate and spaced apart from the delivery device with the proximal terminal free end and the distal terminal free end outside the delivery device and completely within the patient, and to allow the scaffold to expand to anchor the scaffold to tissue surrounding the target tissue;
grasping a free end of a tissue traction element having an opposite terminal end anchored to the scaffold; and
pulling the tissue traction element towards the region of target tissue and coupling a portion of the free end of the tissue traction element to the region of target tissue to exert traction force on the grasped region of target tissue to lift the grasped tissue with respect to surrounding tissue;
wherein the terminal end of the tissue traction element is anchored to the scaffold and anchored in place with respect to the target tissue by the engagement of the scaffold with the tissue surrounding the target tissue without further action required to anchor the tissue traction device with respect to the tissue.

* * * * *